US009747687B2

(12) United States Patent
Tajbakhsh et al.

(10) Patent No.: US 9,747,687 B2
(45) Date of Patent: Aug. 29, 2017

(54) SYSTEM AND METHOD FOR DETECTING POLYPS FROM LEARNED BOUNDARIES

(71) Applicants: ARIZONA BOARD OF REGENTS ON BEHALF OF ARIZONA STATE UNIVERSITY, Scottsdale, AZ (US); MAYO FOUNDATION FOR MEDICAL EDUCATION AND RESEARCH, Rochester, MN (US)

(72) Inventors: Nima Tajbakhsh, Tempe, AZ (US); Suryakanth R. Gurudu, Phoenix, AZ (US); Jianming Liang, Phoenix, AZ (US)

(73) Assignees: Arizona Board of Regents on Behalf of Arizona State University, Scottsdale, AZ (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/305,288

(22) PCT Filed: Apr. 24, 2015

(86) PCT No.: PCT/US2015/027552
§ 371 (c)(1),
(2) Date: Oct. 19, 2016

(87) PCT Pub. No.: WO2015/164768
PCT Pub. Date: Oct. 29, 2015

(65) Prior Publication Data
US 2017/0046835 A1    Feb. 16, 2017

Related U.S. Application Data

(60) Provisional application No. 61/983,868, filed on Apr. 24, 2014.

(51) Int. Cl.
*G06K 9/00* (2006.01)
*G06T 7/00* (2017.01)
(Continued)

(52) U.S. Cl.
CPC ........ *G06T 7/0012* (2013.01); *A61B 1/00009* (2013.01); *A61B 1/0646* (2013.01);
(Continued)

(58) Field of Classification Search
USPC ........ 382/100, 103, 106–107, 128–133, 162, 382/168, 173, 181, 199, 203, 209, 219,
(Continued)

(56) References Cited

U.S. PATENT DOCUMENTS

| 8,184,888 B2 * | 5/2012 | Lu | G06T 7/143 |
| | | | 382/131 |
| 8,369,593 B2 * | 2/2013 | Peng | A61B 6/032 |
| | | | 378/21 |

(Continued)

OTHER PUBLICATIONS

The International Search Report and Written Opinion with a date of mailing of Jul. 31, 2015 for International Application No. PCT/US2015/027552.

*Primary Examiner* — Seyed Azarian
(74) *Attorney, Agent, or Firm* — Quarles & Brady LLP

(57) ABSTRACT

A system and method for automated polyp detection in optical colonoscopy images is provided. In one embodiment, the system and method for polyp detection is based on an observation that image appearance around polyp boundaries differs from that of other boundaries in colonoscopy images. To reduce vulnerability against misleading objects, the image processing method localizes polyps by detecting polyp boundaries, while filtering out irrelevant boundaries, with a generative-discriminative model. To filter out irrelevant boundaries, a boundary removal mechanism is provided that captures changes in image appearance across
(Continued)

polyp boundaries. Thus, in this embodiment the boundary removal mechanism is minimally affected by texture visibility limitations. In addition, a vote accumulation scheme is applied that enables polyp localization from fragmented edge segmentation maps without identification of whole polyp boundaries.

20 Claims, 14 Drawing Sheets

(51) Int. Cl.
*A61B 1/31* (2006.01)
*A61B 1/00* (2006.01)
*A61B 1/06* (2006.01)
*G06T 7/40* (2017.01)
*G06T 7/73* (2017.01)
*G06K 9/46* (2006.01)
*G06K 9/62* (2006.01)
*A61B 6/02* (2006.01)

(52) U.S. Cl.
CPC ............. *A61B 1/31* (2013.01); *G06K 9/4604* (2013.01); *G06K 9/6267* (2013.01); *G06T 7/0085* (2013.01); *G06T 7/40* (2013.01); *G06T 7/73* (2017.01); *G06T 2207/10016* (2013.01); *G06T 2207/10024* (2013.01); *G06T 2207/10068* (2013.01); *G06T 2207/20076* (2013.01); *G06T 2207/30028* (2013.01); *G06T 2207/30032* (2013.01)

(58) Field of Classification Search
USPC ....... 382/232, 254, 274, 276, 287, 291, 305, 382/312; 378/4, 21, 41; 600/332, 343
See application file for complete search history.

(56) References Cited

U.S. PATENT DOCUMENTS

| | | | |
|---|---|---|---|
| 2004/0252882 A1 | 12/2004 | Krumm et al. | |
| 2009/0074270 A1* | 3/2009 | Tanaka | G06K 9/4609 382/128 |
| 2009/0074272 A1* | 3/2009 | Lu | G06T 7/143 382/128 |
| 2010/0189326 A1* | 7/2010 | McGinnis | G06T 7/0012 382/131 |
| 2011/0135180 A1* | 6/2011 | Sugrue | G06T 5/50 382/131 |
| 2011/0206250 A1* | 8/2011 | McGinnis | G06T 7/0012 382/128 |

* cited by examiner

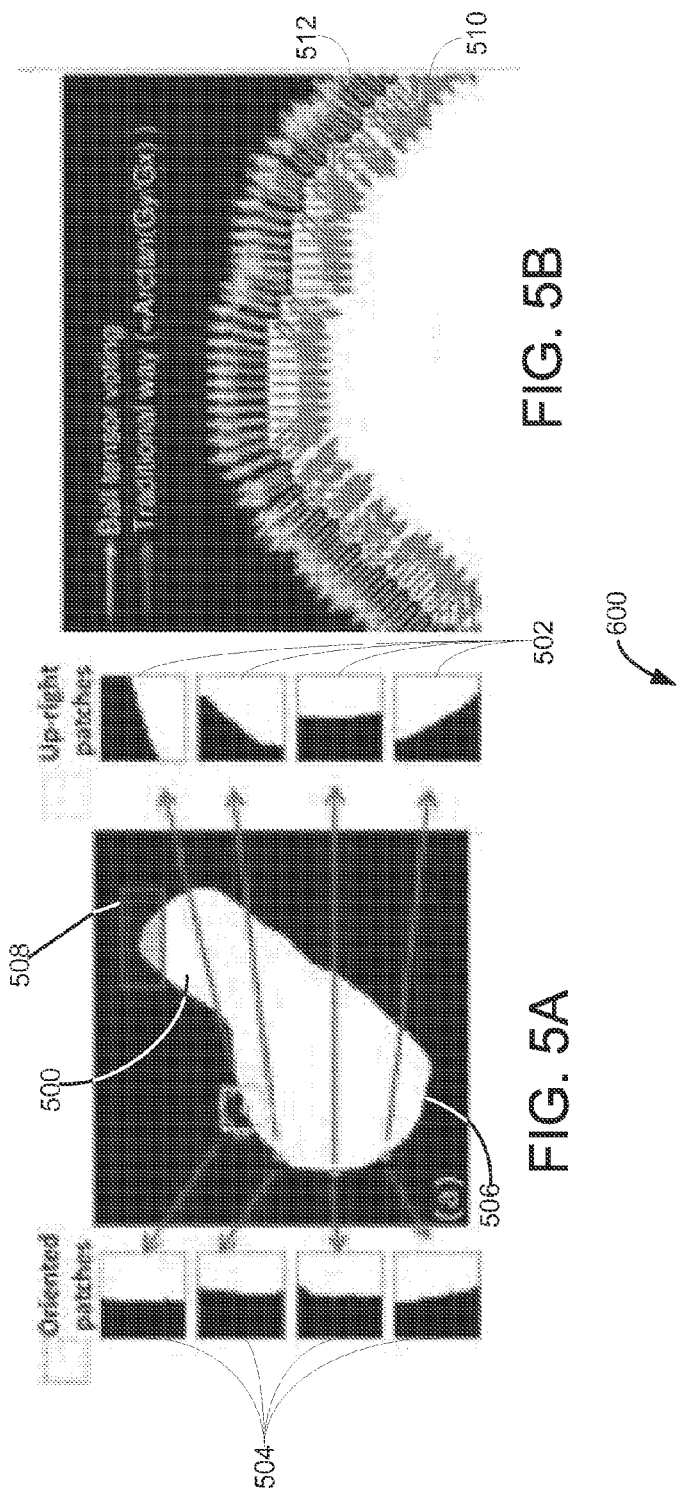
FIG. 5A
FIG. 5B
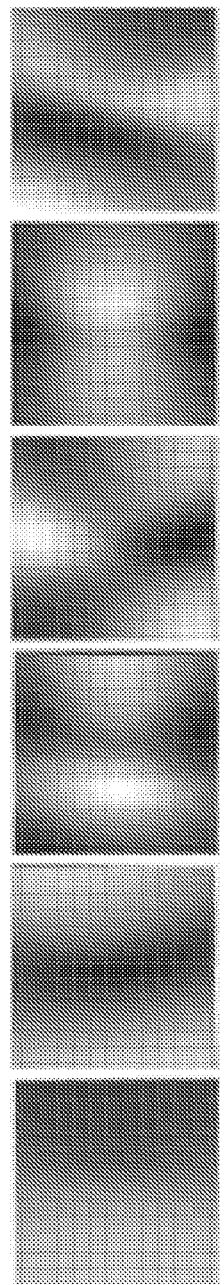
FIG. 6

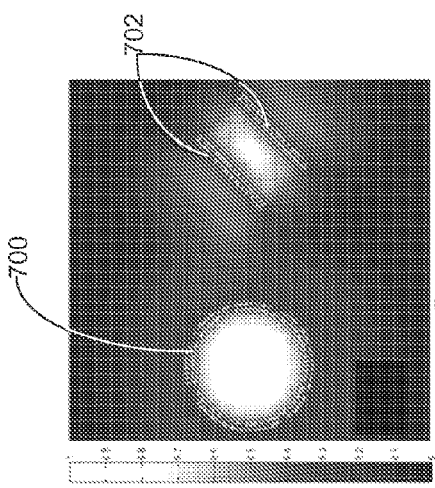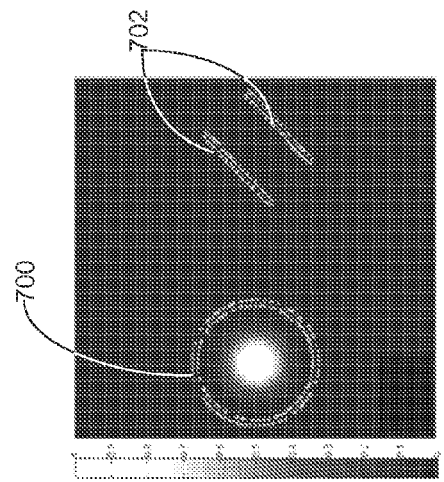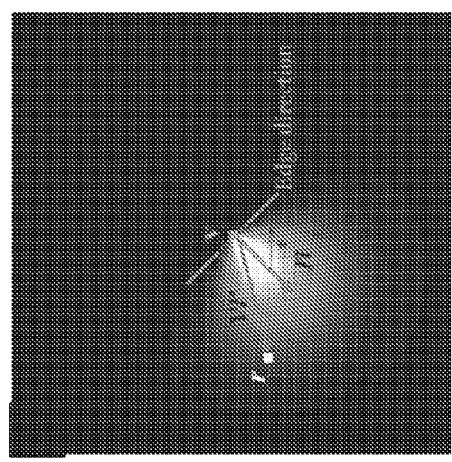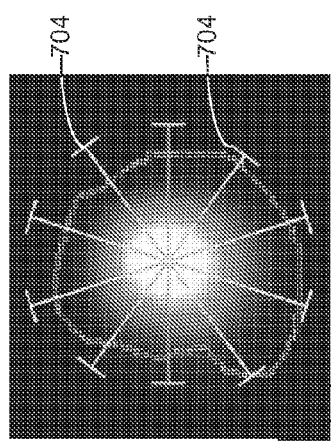

| Recall | Precision | | |
|---|---|---|---|
| | Current Method | Previous work [6] | SA-DOVA [5] |
| 50% | 97% | 90% | 92% |
| 60% | 96% | 88% | 78% |
| 70% | 95% | 89% | 65% |
| 80% | 93% | 86% | 60% |

FIG. 12

| Recall | Precision | | |
|---|---|---|---|
| | Current Method | Previous Work | Bernal[4] |
| | σ=70 σ=100 | | |
| 50% | 98% 100% | 90% | 92% |
| 60% | 97% 98% | 88% | 78% |
| 70% | 96% 95% | 89% | 65% |
| 80% | 94% 92% | 86% | 60% |

FIG. 13

SYSTEM AND METHOD FOR DETECTING POLYPS FROM LEARNED BOUNDARIES

CROSS-REFERENCE TO RELATED APPLICATIONS

This application represents the national stage entry of PCT International Application No. PCT/US2015/027552 filed on Apr. 24, 2015 and claims priority from U.S. Patent Application No. 61/983,868 filed Apr. 24, 2014.

STATEMENT REGARDING FEDERALLY SPONSORED RESEARCH

N/A

BACKGROUND

The subject matter described herein relates to systems and methods for processing optical images, and, more particularly, to automatic detection of polyps in optical images.

Colorectal cancer (CRC) is the second highest cause of cancer-related deaths in the United States with 50,830 estimated deaths in 2013. More than 80% of CRC cases arise from adenomatous polyps, which are precancerous abnormal growths of the colon wall. The preferred screening method for polyp detection and removal is an optical colonoscopy (OC) procedure, during which a colonoscopist meticulously examines the colon wall using a tiny camera that is inserted and guided through the colon. The goal of an OC is to detect and remove colorectal polyps, which may be precursors to CRC. Thus, it has been shown that timely removal of polyps can significantly reduce the mortality of CRC.

However, polyp detection with OC remains a challenging task and, as evidenced by several clinical studies, a significant portion of flat and pedunculated polyps remain undetected during colon screening with OC. High polyp detection rate requires a high level of attentiveness, alertness, and sensitivity to visual characteristics of polyps from colonoscopists and such qualities may only be procured after years of practice and experience. It is therefore important to reduce polyp miss-rate as it decreases the incidence and mortality of CRC.

Computer-aided polyp detection has recently been considered as a tool for reducing polyp miss-rate. For example, during an OC procedure, regions with suspected polyps can be highlighted for further examination. Existing approaches for polyp detection primarily rely on the shape or texture of polyps. However, shape information is susceptible to partial and fragmented image segmentation and can mislead a detector towards irrelevant objects in the complex endoluminal scene. Texture may also be unreliable because its visibility depends on camera-polyp distance. Thus, the texture of a polyp becomes fully visible only when the camera captures close shots of the surface of a polyp. This condition is often met when polyps have already been detected by operators. On the other hand, shape information cannot be considered as a reliable measure because polyps appear in a variety of forms ranging from sessile to peduncular shapes. Therefore, texture-based and shape-based polyp detectors offer limited practical value.

Consequently, considering such limitations of previous technological approaches, it would be desirable to have a system and method for accurate and reliable polyp detection in optical colonoscopy images that is shape-based and can compensate for the concomitant drawbacks of shape-based detection.

SUMMARY

In accordance with one aspect, a system for automated polyp detection in optical colonoscopy images is disclosed. The system includes an input configured to acquire a series of optical images, a processor, and a memory. The memory contains instructions that, when executed by the processor, causes the processor to perform a process on the series of optical images. The processor applies a color filter to create a plurality of color filtered images for each optical image of the series of optical images, and locates a series of edge pixels on at least one of the plurality of color filtered images. The process then obtains a plurality of oriented image patches corresponding to each of the series of the edge pixels. The plurality of oriented image patches are represented by an intensity signal characterized by at least one of rotation invariance or illumination invariance. An edge normal for each edge pixel is then estimated. At least one classification system is constructed corresponding to the plurality of color filtered images. The at least one classification system is configured to enhance low level features of the plurality of color filtered images prior to classification, and appearance features are generated from a series of feature vectors selected from the classification system. An edge classification threshold analysis is then performed on each of the plurality of oriented image patches. Based on the edge classification threshold analysis, the processor determines that a given image patch is consistent with an edge threshold. A report is generated indicating potential polyps with a vote accumulation greater than a threshold. The vote accumulation includes a probabilistic output for each of the potential polyps in the absence of a predefined parametric model.

In accordance with another aspect, a method for automated polyp detection in optical colonoscopy images is disclosed. The method includes applying a color filter to create a plurality of color filtered images for each of a plurality of optical images. A series of edge pixels are located on at least one of the plurality of color filtered images, and a plurality of oriented image patches are obtained corresponding to each of the series of the edge pixels. The plurality of oriented image patches are represented by an intensity signal characterized by at least one of rotation invariance or illumination invariance. An edge normal is estimated for each edge pixel, and at least one classification system is constructed corresponding to the plurality of color filtered images. The at least one classification system is configured to enhance low level features of the plurality of color filtered images prior to classification. Appearance features are generated from a series of feature vectors selected from the at least one classification system, and an edge classification threshold analysis is performed on each of the plurality of oriented image patches. Based on the edge classification threshold analysis, a given image patch is determined to be consistent with an edge threshold. A report is generated indicating potential polyps with a vote accumulation greater than a threshold. The vote accumulation includes a probabilistic output for each of the potential polyps in the absence of a predefined parametric model.

The foregoing and other aspects and advantages of the disclosure will appear from the following description. In the description, reference is made to the accompanying drawings which form a part hereof, and in which there is shown by way of illustration one embodiment. Such embodiment does not necessarily represent the full scope of the disclosure, however, and reference is made therefore to the claims and herein for interpreting the scope of the disclosure.

BRIEF DESCRIPTION OF THE DRAWINGS

FIG. 5A is an illustration showing a ground truth of a polyp and corresponding upright and oriented image patches along the edge direction.

FIG. 5B is an illustration showing estimated edge normals using a gradient-based approach and a ball tensor approach for the region highlighted in FIG. 5A.

FIG. 6 is a series of six eigen images selected from a two-stage classification system.

FIG. 7A is a geometric illustration of a voting scheme for an edge pixel lying at 135 degrees.

FIG. 7B is an illustration of an original voting map for parallel and circular edges.

FIG. 7C is an illustration of a modified voting map for parallel and circular edges.

FIG. 7D is an illustration of a voting map for a polyp showing search radii for a subset of radial rays.

FIG. 12 is a precision recall of polyp detection table comparing various polyp detection systems.

FIG. 13 a precision recall of polyp detection table comparing various polyp detection systems.

DETAILED DESCRIPTION

Figure 1:
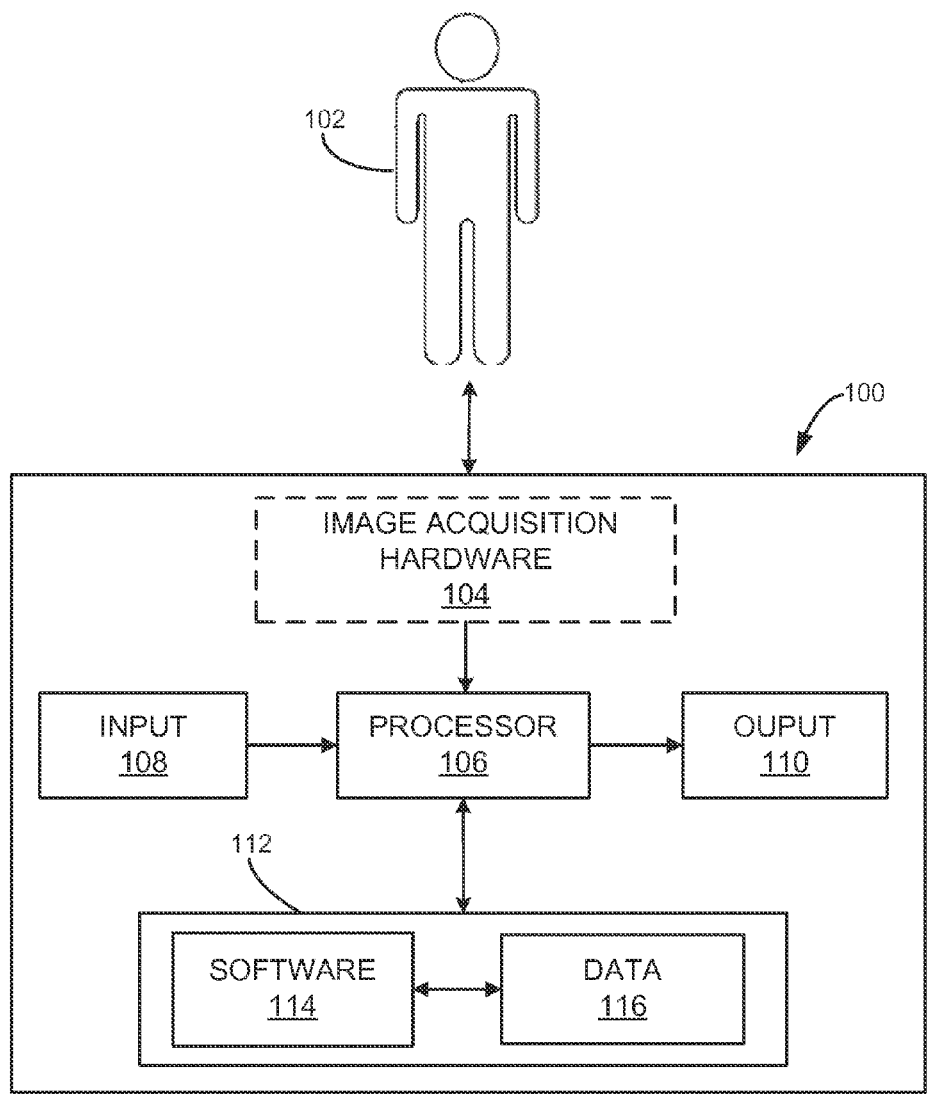
FIG. 1 is a schematic illustration of an exemplary system for polyp detection in optical colonoscopy images in accordance with the present disclosure.

The present disclosure describes embodiments that overcome the aforementioned drawbacks by providing a system and method for polyp detection based on an observation that image appearance around the polyp boundaries differs from that of other boundaries in colonoscopy images. To reduce vulnerability against misleading objects, the imaging processing method localizes polyps by detecting polyp boundaries, while filtering out irrelevant boundaries, with classification and feature extraction methods. To filter out irrelevant boundaries, a boundary removal mechanism is provided that captures changes in image appearance across polyp boundaries. Thus, the boundary removal mechanism is minimally affected by texture visibility limitations. In addition, the present disclosure describes embodiments that overcome the challenges posed by partial polyp segmentation by applying a vote accumulation scheme that enables polyp localization from fragmented edge segmentation maps without requiring perfect identification of whole polyp boundaries and knowledge about shapes and size of polyps. Therefore, the systems and methods as described herein assist both experienced, and inexperienced, colonoscopists with accurately detecting and locating polyps.

In addition, the present disclosure describes embodiments that overcome the aforementioned drawbacks by providing a system and method for polyp detection that combines image context with shape information to minimize the misleading effect of irrelevant objects with polyp-like boundaries. Given an input image, the present method begins with collecting a crude set of boundary pixels that are refined by a patch descriptor and classification scheme, before feeding a voting scheme for polyp localization. The patch descriptor quickly and efficiently characterizes image appearance across object boundaries, and is both rotation invariant and robust against linear illumination changes. A two-stage classification framework is also provided that is able to enhance low level image features prior to classification. Unlike traditional image classification where a single patch undergoes the processing pipeline, the present system fuses the information extracted from a pair of patches for more accurate edge classification. In addition, a vote accumulation scheme that robustly detects objects with curvy boundaries in fragmented edge maps is provided. The voting scheme produces a probabilistic output for each polyp candidate, but does not require any predefined parametric model of polyps (e.g., circle and ellipse).

Thus, the disclosed polyp detection system and method are based on two key observations. First, polyps, irrespective of their morphology, feature a curvy segment in their boundaries. The polyp detection system uses this property to localize polyps by detecting objects with curvy boundaries. Second, image appearance across the polyp boundaries is highly distinct from that of vessels, lumen, and specular reflections. Thus, present patch descriptor and classification scheme is able to distinguish polyp boundaries from the boundaries of other colonic objects, producing a refined edge map for the vote accumulation scheme.

The methodology of the present disclosure is based on image appearance variation between polyps and their surrounding tissue. The rationale takes into account that local patterns of color variation across the boundary of polyps differ from the patterns of color variation that occur across the boundary of folds, lumen, and vessels.

Turning to FIG. 1, a block diagram is shown of an exemplary polyp detection system 100, which facilitates the detection of polyps on optical images gathered from a subject 102. The polyp detection system 100 generally may include image acquisition hardware 104, a processor 106, an input 108, an output 110, a memory 112, and any device for reading computer-readable media (not shown). The polyp detection system 100 may be, for example, a workstation, a notebook computer, a personal digital assistant (PDA), a multimedia device, a network server, a mainframe or any other general-purpose or application-specific computing device. The polyp detection system 100 may operate autonomously or semi-autonomously, or may read executable software instructions from a computer-readable medium (such as a hard drive, a CD-ROM, flash memory and the like), or may receive instructions from a user, or any another source logically connected to a computer or a device, such as another networked computer or server. In one embodiment, the polyp detection system 100 is configured to acquire and analyze optical image data in real-time from a live feed, while a medical procedure is being performed on a subject 102, such as a colonoscopy, and is also configured to retrieve and analyze optical image data already acquired and stored in any image data storage location.

The image acquisition hardware 104 may be designed to acquire optical image data continuously or intermittently, for example, during a medical procedure, such as a colonoscopy, and relay optical image data for processing. The image acquisition hardware 104 may require operator direction, input or feedback, or may be designed to operate autonomously.

The processor 106 may be configured to process optical image data, including image data obtained during a medical procedure, such as a colonoscopy. In one embodiment, the processor 106 may be designed to process optical images, generated from optical image data, by applying a plurality of color filters. One non-limiting example of a plurality of filters may include a red (R), green (G) and blue (B) filter, often referred to as an RGB filter. Within this example, an hue-saturation-lightness (HSL) or hue-saturation-value (HSV) coordinate representation of the RGB model may be used. Other non-limiting examples of color maps include La*b* (or Lab color space). In addition, it is possible to use more than one color map, for instance, RGB+La*b*. Regardless of the filter, map, color space, particular combination of filters, maps, or color spaces, the present disclosure provides a system and method for polyp detection that leverages the appearance of color variation between polyps and surrounding tissues.

The input 108 may take any suitable shape or form, as desired, for operation of the polyp detection system 100, including the ability for selecting, entering or otherwise specifying parameters consistent with detecting polyps of a requisite or desired size or shape.

The output 110 may take any suitable shape or form, as desired, and may include a visual and/or audio system, configured for displaying, for example, acquired optical images as a result of a medical procedure, such as a colonoscopy, and also configured, for example, to highlight and/or alert an operator of the polyp detection system 100 upon identification of a polyp with the requisite or desired features.

The memory 112 may contain software 114 and data 116, and may be configured for storage and retrieval of image processing information and data to be processed by the processor 106. In one embodiment, the software 114 includes instructions directed to performing optical image processing for polyp detection. In another embodiment, the data 116 includes optical image data.

Figure 2:
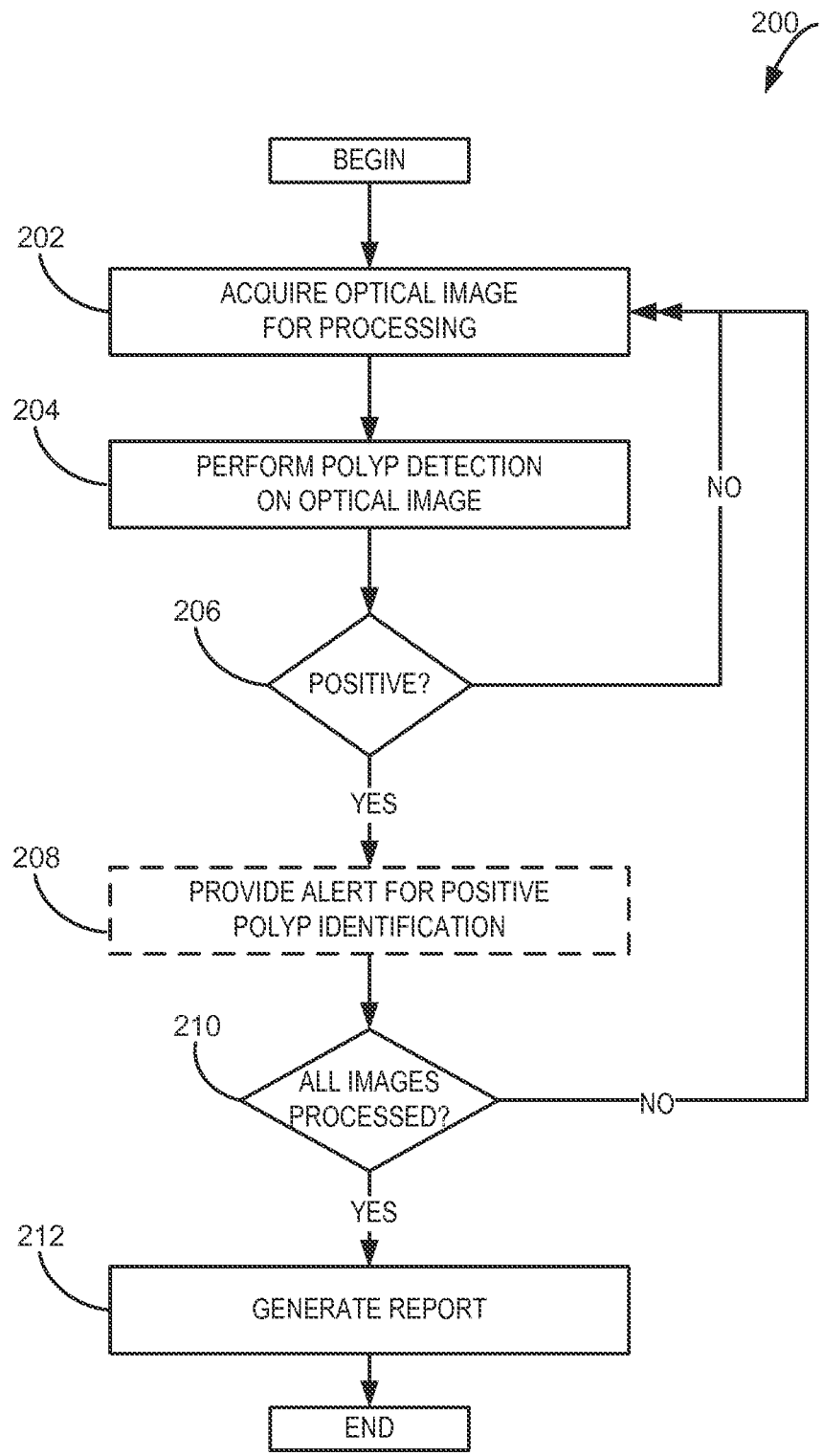
FIG. 2 is a flowchart setting forth steps of an exemplary method of operating an automated polyp detection system in accordance with the present disclosure.

Turning to FIG. 2, a process 200 flowchart is shown illustrative of an exemplary method of operation for a polyp detection system 100. The process begins at process block 202, wherein optical image data generated from a live feed, or retrieved from any image data storage location, such as the memory 112, is acquired in the form of an optical image by the polyp detection system 100. At process block 204, a polyp detection is performed on the optical image.

Figure 3:
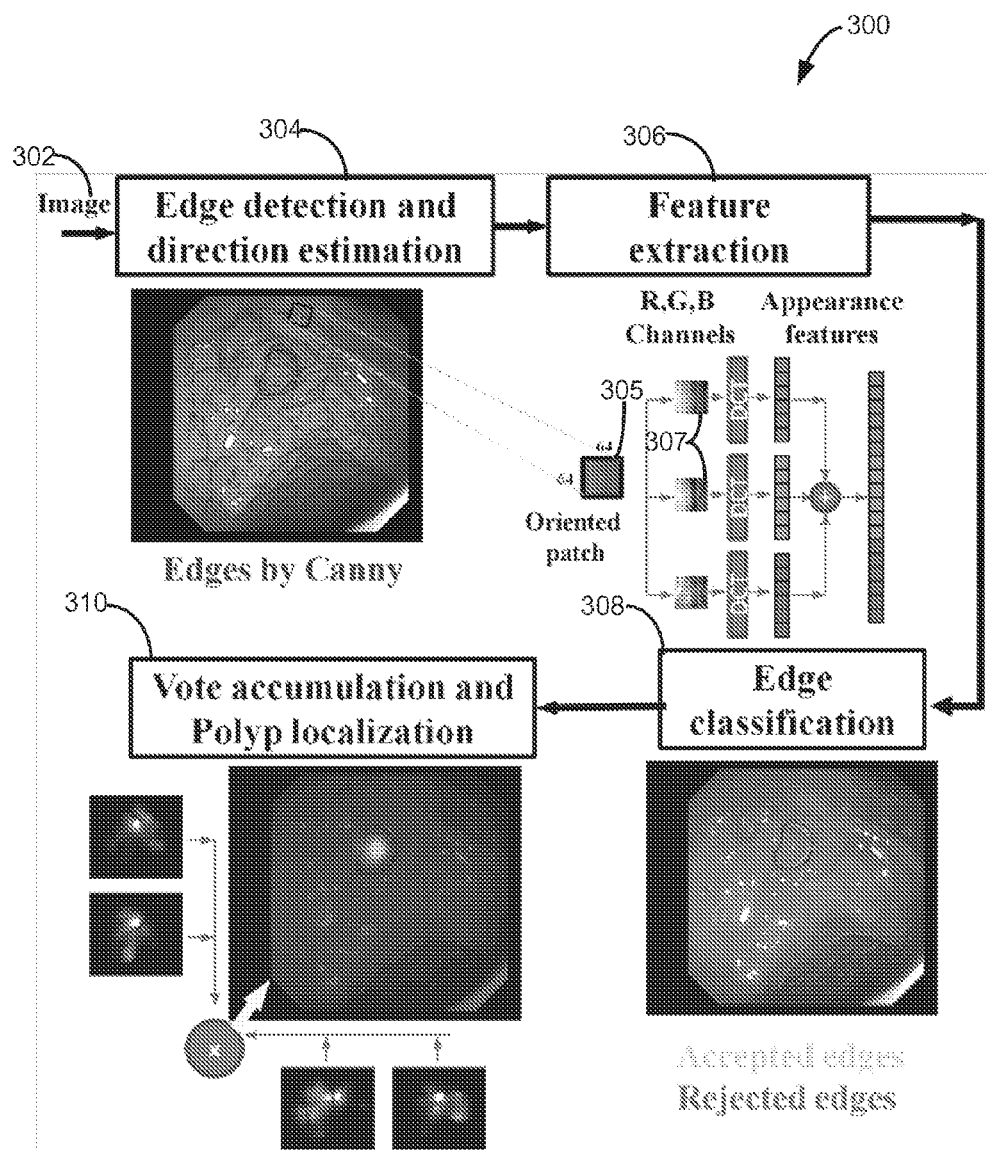
FIG. 3 is a schematic illustration of a process for automated polyp detection in optical colonoscopy images in accordance with the present disclosure.

Illustrating the general steps associated with performing the polyp detection of process block 204, is a flow diagram shown in FIG. 3. The polyp detection process 300 begins with an optical image 302, which undergoes an edge detection and edge direction estimation at process block 304, wherein a crude set of edge pixels are generated to form a corresponding crude edge map using any suitable edge detector, such as a Canny edge detector. In some embodiments, the Canny edge detector is replaced by a raster scan, however this approach may yield increased computational costs. Thus, because the primary goal is to detect polyp edges, the edge detector may be utilized to limit the search space to a small subset of image pixels.

Next, at process block 306, image patches 305 of polyp boundaries are captured by extracting oriented sub-images 307 along the edge normals that correspond to the R, G, and B color channels. The feature extraction method is then applied on the oriented sub-images 307 to generate appearance features. Next, at process block 308, the crude edge map is refined by means of a classification scheme that operates on the extracted features. More specifically, a two-stage classification system is used to filter out irrelevant, non-polyp edges (e.g., those edges lying on folds and vessels), while retaining edges around and on the polyp boundary. By filtering out the irrelevant boundaries, the change in image appearance across the boundary of polyps is revealed, which differs from what is observed across other boundaries. Thus, image patches 305 that are extracted from polyp boundaries may be referred to as "positive patches" and the remaining image patches as "negative patches." Similarly, the edges that lie on the boundary of polyps may be referred to as "polyp edges" and the remaining edges may be referred to as "non-polyp edges." Once the crude edge map is refined, at the next process block 310, a vote accumulation scheme is applied to the refined map to localize polyps.

Figure 4:
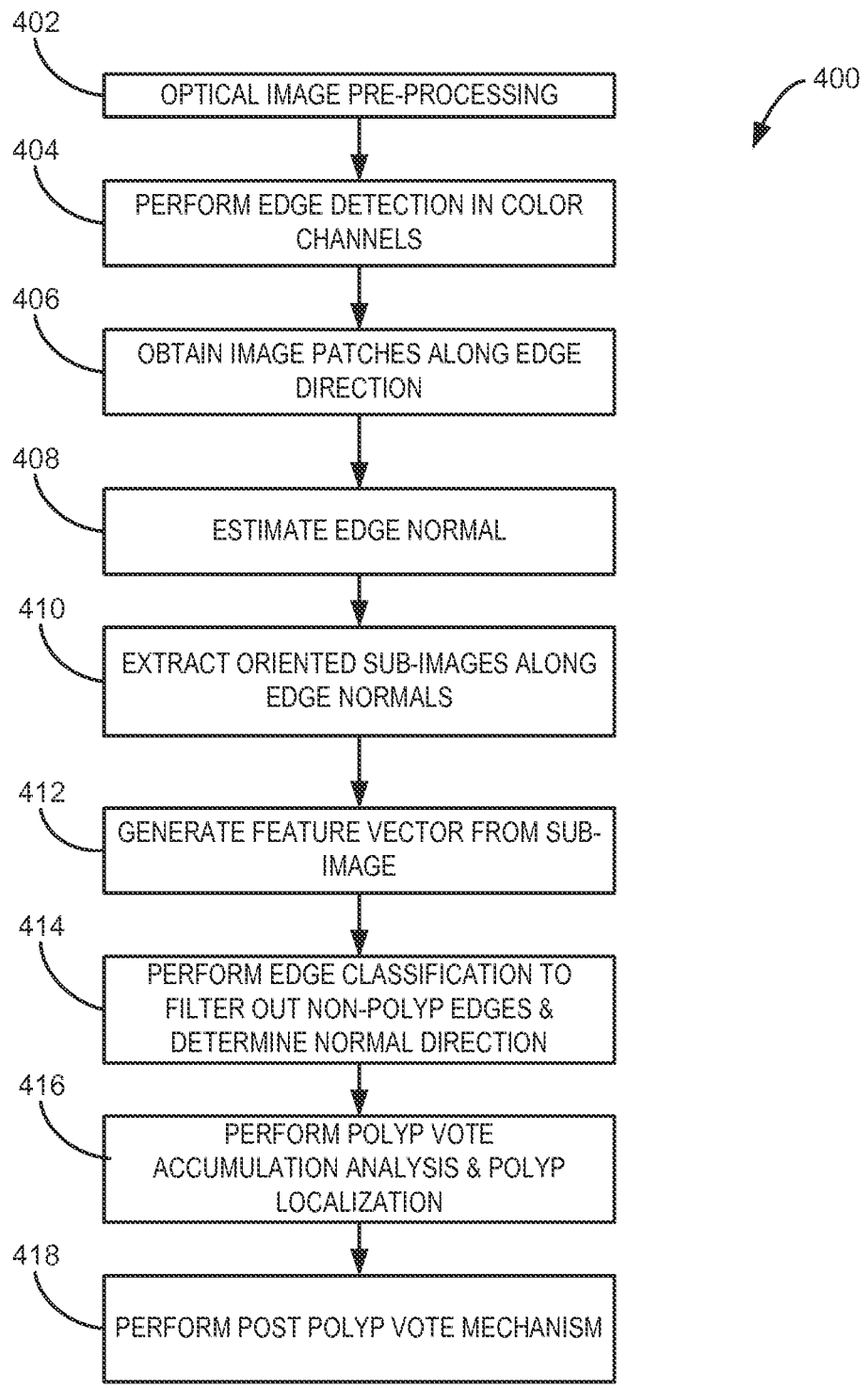
FIG. 4 is a flowchart setting forth steps of an exemplary method for polyp detection in accordance with the present disclosure.

FIG. 4 illustrates an exemplary method for polyp detection. Referring to FIG. 4, the polyp detection process 400 begins at process block 402, where a number of pre-processing steps may be applied to the optical image 302, including Gaussian smoothing and/or color filtering. Heavy Gaussian smoothing at process block 402 may remove a large portion of edge pixels including those on the boundaries of polyps. By contrast, slight smoothing may include both prominent and irrelevant edges, which not only may pose a large computational burden on the later stages, but also may increase the chance of producing false positives. Hence, a standard deviation of the Gaussian function may be set to 3 ($\sigma_g=3$) to achieve both sensitivity against polyp edges and computational efficiency, although other values are possible.

Edge Detection

Then, at process block 404, a crude set of edge pixels are detected in order to characterize image appearance across polyp boundaries. To do so, any suitable edge detection method, such as a Canny's method, is applied on the three color channels of the input images to extract as many edges as possible. The goal is to obtain an overcomplete edge map which will further be refined through a classification scheme.

Edge Direction Estimation

Next, at process block 406, oriented image patches are extracted along the edge direction. Particularly, as shown in FIG. 5A, the ground truth of a polyp region 500 is shown having corresponding upright image patches 502 and corresponding oriented image patches 504 for four selected edges on a boundary 506 of the polyp region 500. The ground truth is a binary image whose white pixels indicate the polyp region 500 and black pixels represent the background region, as shown in FIG. 5A. While the polyp region 500 can appear in any portion of the upright patches 502, the polyp region 500 only appears on the right side of the oriented image patches 504.

Next, at process block 408, a robust and accurate estimation of edge normal may be computed. The normal directions are used to extract oriented patches around the edges. In certain embodiments, an accurate estimate of edge normal is important to collecting sound oriented patches 504. In some cases, edge normals computed using a gradient-based approach are often inaccurate, resulting in a non-smooth map of edge normal and poorly aligned image patches. For example, as shown in FIG. 5B, estimated edge normals for the region highlighted with the rectangle 508 in FIG. 5A are shown using a gradient-based approach 510 and a tensor voting approach 512. As shown in FIG. 5B, the gradient-based approach 510 yields an inaccurate estimation of edge normals, leading to poorly aligned oriented patches. However, the tensor voting approach 512 operates very reliably except for edges lying on junctions, whose misalignment effects can be mitigated with subsequent classification and voting. The tensor voting approach 512 assumes that a ball tensor is placed at each boundary pixel. In ball tensor voting, edge normal at a pixel is determined according to the arrangement of the surrounding edge pixels such that the continuation of edge normal is maintained.

Feature Extraction and Classification

To capture the unique image appearance of polyps along the boundaries of the polyps, oriented sub-images, for example of size 64×64, may be extracted along the edge normals, as shown at process block 410. As a result, in the extracted sub-images, the edges appear vertically in the middle. For example, an edge pixel at angle θ, may include two possible normals (i.e., $\theta-\pi/2$ and $\theta+\pi/2$) that give two horizontally mirrored sub-images.

Patches, for example of size 8×16, are formed all over each sub-image with about 50% overlap along horizontal and vertical directions. Each patch may then be averaged vertically, resulting in a 1-dimensional (1D) intensity signal which presents intensity variation along the horizontal axis. A 1D discrete cosine transform (DCT) may then be applied to obtain a compact and informative presentation of the signal. To achieve invariance against constant illumination changes, the DC component (i.e., the average patch intensity) is discarded. To achieve invariance against linear illumination scaling, the AC coefficients may be divided by the norm of the DCT coefficients vector. Thus, the descriptor can partially tolerate nonlinear illumination change over the whole sub-image, particularly if the nonlinear change can be decomposed to a set of linear illumination changes on the local patches. Then, the first few normalized AC coefficients may be selected from each patch corresponding to low frequency intensity changes and concatenated to form a feature vector for a sub-image, as shown at process block 412.

The above described image descriptor provides rotation invariance, which is important because features that can consistently represent image appearance across edges lying at arbitrary directions are needed. In addition, the image descriptor provides illumination invariance, which is important in colonoscopy since the source of light moves along with the camera, thereby causing the same segment of a polyp boundary to appear with varying contrast in different frames.

In an alternative embodiment, image patches of polyp boundaries are obtained and oriented in order to construct principal component analysis (PCA) models that correspond to the R, G, and B color channels. To fully utilize the information content of color patches, three PCA models corresponding to R, G, and B color channels may be constructed. Eigenvectors are then selected from each of the three PCA models such that approximately 90% of the total eigenvalue sum is covered, resulting in a 60-dimensional feature space. To generate appearance features, each image patch is projected along the selected eigenvectors and the resultant projection coefficients are concatenated to form the feature vectors. Compared to general purpose features, such as Haar and steerable filters, PCA eigen images 600, as shown in FIG. 6, allow the patterns of interest to be represented in a lower dimensional feature space. More importantly, PCA naturally handles feature selection according to the corresponding eigen values, which obviates the need for employing sophisticated feature selection methods. The crude edge map is refined by means of a classification model. More specifically, a random forest classifier is used to filter out irrelevant, non-polyp edges (e.g., those edges lying on folds and vessels), while retaining edges around and on the polyp boundary.

Returning to FIG. 4, at process block 414, an edge classification is performed to refine an edge map by filtering out "non-polyp" edges and to determine the normal direction for the retained polyp-like edges, such that the normals point toward polyp locations. To achieve these objectives, a two-stage classification system may be implemented where the first stage produces mid-level image features from low-level input features, while the second stage learns both edge label (i.e., "polyp or "non-polyp") and normal direction. The classification system further includes labeling of sub-negative classes, which can be done either manually or in an unsupervised way by applying Kmeans on negative patches.

To train the first layer, $N_1$ oriented patches may be collected around boundaries of polyps and four sub-negative classes: vessels, lumen areas, specular reflections, and around edges at random locations in training images. A five-class classifier may be trained using the patch descriptor. The output of the classifier may be an array of probabilities for the five object classes. Compared with the low level input features, which encode local image variation, the generated output array contains mid-level features that measure the global similarity between the underlying input sub-image and the general appearance of the predefined structures.

To train the second layer, $N_2$ pairs of oriented patches may be collected from polyp boundaries and other random locations in training images. In one non-limiting example, let $\{p_i^1, p_i^2\}$ be the extracted pair of patches around $i^{th}$ edge with the corresponding normals, $\{n_i^1, n_i^2\}$, where $\angle n_i^1 \in [0,\pi)$ and $\angle n_i^2 = \angle n_i^1 + \pi$. Based on the state of the $i^{th}$ edge, a label, $y_i \in \{0, 1, 2\}$ may be assigned to each pair of patches, where "0" is for a non-polyp edge, "1" is for a polyp edge with normal being $n_i^1$, and "2" is for a polyp edge with normal being $n_i^2$. Such labeling is possible given the ground truth for polyps. Next, low level features may be extracted from each pair of patches and the classifier trained may be applied in the first layer, resulting in two arrays of mid-level features per pair that are further concatenated to form a feature vector, $\{f_i, y_i\}$. Once the feature vectors are collected, a three-class classifier may be trained to learn both edge label and edge normal direction. In the test stage, the label with maximum probability may be assigned to the underlying edge pixel.

More generally, the second layer of classification fuses knowledge captured from a pair of patches because combining the two sources of information can yield more accurate edge classification. For example, if the patch $p_i^1$ around the $i^{th}$ edge resembles the appearance of a polyp, and the counterpart patch $p_i^2$ looks very similar to the average appearance of specular reflections or lumen areas, it may be difficult to determine the underlying edge pixel. In one embodiment, the first patch may be relied on and a polyp edge with edge normal being $n_i^1$ may be declared. In another embodiment, information from the counterpart patch may be considered and a non-polyp edge may be declared. In yet another embodiment, to determine the underlying pixel, a second classifier in the mid-level feature space may be trained to fully utilize such relationships.

Vote Accumulation for Polyp Localization

At the next process block 416, a polyp vote accumulation analysis is performed. In the ideal classification scenario, all non-polyp edge pixels are removed and the arrangement of positive pixels indicates the locations of polyps. However, in practice, a portion of non-polyp edges may pass the classification stage and induce false positives. On the knowledge that false positive edges often appear on elongated and low-curvature edge segments, a vote accumulator scheme that will mitigate the effect of false positive edges, but also enable polyp localization from fragmented edges, may be utilized. The vote accumulation scheme assigns high values to the regions that are partially surrounded by curvy edges, but gives low values to the regions that are surrounded by elongated low curvature edges.

Turning to FIG. 7A, in a vote accumulator scheme, the edges that have passed the classification stage may be referred to as "voters." Each voter includes a polyp direction $n_i^*$ and a classification confidence $C_{vi}=\max(p(y^i=1), p(y^i=2))$. The voting scheme begins with grouping the voters into K categories according to the voting directions of the voters, $$V^k = \left\{ v_i \;\middle|\; \frac{k\pi}{K} < \angle n_i^* < \frac{(k+1)\pi}{K} \right\}, k = 0 \ldots K.$$

Such edge grouping prior to vote casting minimizes vote accumulation in the regions that are surrounded by low curvature boundaries. The voters in each category then cast votes at their surrounding pixels according to their voting directions and classifications confidence. This results in K voting maps that are further multiplied to form the final voting map whose maximum vote accumulation (MVA) indicates the location of a polyp candidate, as shown the equation below:

$$MVA = \underset{x,y}{\arg\max} \prod_{k=1}^{K} \sum_{v \in V_k} M_v(x, y), \quad \text{Eqn. (1)}$$

where $M_v(x, y)$ is the vote cast by the voter v at a receiver pixel $r=[x, y]$, which is computed as follows:

$$M_v(r) = \begin{cases} C_v \exp\left(\frac{-\|\vec{vr}\|^2}{\sigma}\right) \cos(\angle n^* \vec{vr}), & \text{if } \angle n^* \vec{vr} < \pi/2 \\ 0, & \text{if } \angle n^* \vec{vr} \geq \pi/2 \end{cases} \quad \text{Eqn. (2)}$$

where σ controls the size of the voting field. FIG. 7A shows the voting field for an edge pixel lying at 135 degree. As shown, the votes are cast in the region pointed by the voting direction. Such selectivity arises from the condition set on $\angle n^* \vec{vr}$, which inhibits the voters from casting votes in the opposite direction. The exponential and cosinusoidal decay functions enable smooth vote propagation, which may be used to determine the likelihood of a polyp candidate.

However, in the accumulation scheme described above, votes received at each pixel are accumulated irrespective of the voters' orientation. This implies that the proposed accumulator may be undesirably sensitive to any accumulation of votes, no matter whether they are received from the edge pixels forming a circle or from the edge pixels arranged on parallel lines. Thus, regions delineated by parallel edge segments or by low curvature counters, in general, may not represent polyps. High responses in such regions may result in false positive detections.

As shown in FIG. 7B, the voting map of the edge pixels arranged on a circle 700 is compared to the voting map of the edge pixels lying on two parallel lines 702. Thus, votes are accumulated in two regions, namely, inside the circular edges which is desirable, and between the parallel lines which is undesirable.

To overcome this problem, a constraint may be imposed on the voting scheme, such that regions can attain high accumulated votes if they receive adequate votes from voters whose normal directions span a wide range of [0, 2π), for example. Thus, regions surrounded by low curvature boundary receive low accumulation, because the edge normal of their surrounding voters can only partially cover the range of [0, 2π). Despite the proper handling of low curvature boundaries, this constraint undesirably weakens vote accumulation for the polyps that partially appear behind the folds or close to image borders. In such cases, polyps are segmented incompletely and, thus, the angular range of interest is only covered partially.

To alleviate the above problem, normal directions from [0, 2π) to [0, π), for example, can be mapped and a constraint can be placed on its maximum coverage. This allows for detecting semi-elliptical structures in edge maps. To measure the coverage, normal directions can be discretized into four values, for example. Mathematically, this may be expressed as:

$$\theta^i = i\frac{\pi}{8} \;\middle|\; i = \{1, 3, 5, 7\} \quad \text{Eqn. (3)}$$

In one non-limiting example, the edge normal in the ranger of $$\left(0, \frac{\pi}{4}\right]$$

is mapped to $$\frac{\pi}{8},$$

the edge normal in the range of $$(\frac{\pi}{4}, \frac{\pi}{2}]$$

is mapped to $$\frac{3\pi}{8},$$

and so on. The positively classified edges may then be categorized into four categories according to the quantized values, and the voting process can be performed four times. Each time the voting process is performed, the edge pixels of one specific category are allowed to vote. As illustrated by process block 310 of FIG. 3, the resultant number of, for example, four, voting maps are later multiplied to generate a final voting map.

Turning now to FIG. 7C, the effect of the modified voting map for the same edge pixels is shown. The modified scheme assigns low values to the region between the parallel lines, and high values to the region inside the circular edges. The parameter of the voting scheme is the size of voting field controlled by $\sigma_v$, which can be automatically adjusted given the size of the image and the upper and lower bounds on polyp/image size ratio.

Returning to FIG. 4, a post polyp voting mechanism may be performed at process block 418. To assign a probability to a polyp candidate, a ray back projection may be performed in which radial rays are cast from the detection location outward in all possible directions and then the fraction of rays hitting the voters is calculated. The ray back projection may be used to determine the search radius for each individual ray. Short or long radii may underestimate or overestimate the polyp likelihood. Search radius may be estimated by modeling the decay in vote accumulation along each radial ray. For a ray at angle θ, the search radius is estimated as $3\sigma_\theta$ where $\sigma_\theta$ is the standard deviation of the Gaussian function fitted to the corresponding decay signal. As shown in FIG. 7D the outwardly extending lines represent search radii 704 for a subset of radial rays. Once search radii 704 are determined, the probability of a polyp candidate is measured as $$\frac{1}{180}\sum_{\theta=0}^{179}(R_\theta \vee R_{\theta+180});$$

where $R_\theta$ is an indicator variable that takes 1 if the ray at angle θ hits at least 1 voter, and 0 otherwise.

Figure 8B:
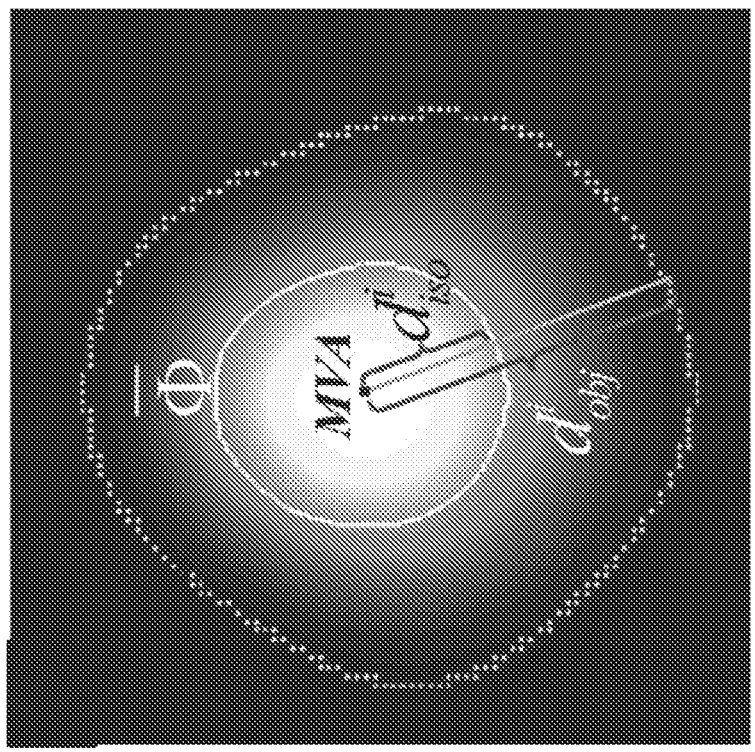
FIG. 8B is an illustration of a representative isocontour $\bar{\Phi}$ of the voting map of FIG. 8A that is used to determine the shape and width of a corresponding narrow band.
Figure 8A:
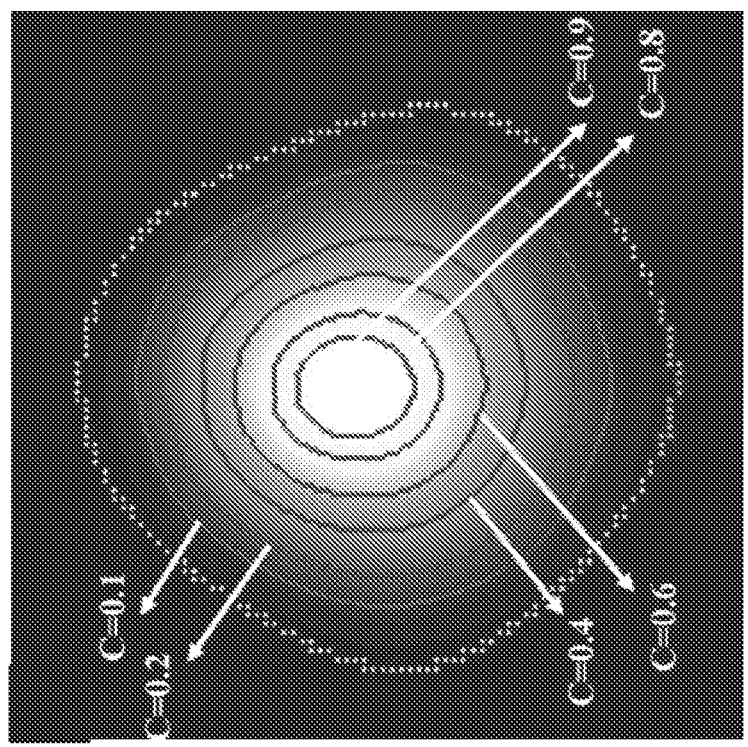
FIG. 8A is an illustration of another voting map having isocontours generated for a synthetic shape.

In an alternative embodiment, the post polyp voting mechanism performed at process block 418 may include defining isocontours of a voting map and then using the isocontours to estimate the unknown parameters of the bands. The isocontour $\Phi_c$ of the voting map V may be defined as $\Phi_c = \{(x, y) | V(x, y) = cM\}$ where M denotes the maximum of the voting map and c is a constant between 0 and 1. The isocontours of a voting map can predict where actual object boundary is through a regression model. Since isocontours may get corrupted by other nearby voters in the scene, several isocontours may be obtained, as shown in FIG. 8A, and then take their median shape as the representative isocontour $\overline{\Phi}$ of the voting map, as shown in FIG. 8B. Let $d_{iso}^i$ denotes the distance between the $i^{th}$ point on $\overline{\Phi}$ and MVA. $d_{iso}^i$ may be used to predict $d_{obj}^i$, the distance between the corresponding point on the object boundary and the MVA within a prediction interval. For this purpose, a second order polynomial regression model $d_{obj}^i = b_0 + b_1(d_{iso}^i) + b_2(d_{iso}^i)^2$ may be used, where $b_0$, $b_1$, and $b_2$ are the regression coefficients and are estimated using a least square approach. Once the model is constructed, the output of the model $d_{obj}$ is taken at angle θ with respect to MVA as $t_\theta$ and the corresponding prediction interval as the bandwidth δ. With this information, the band around the polyp candidate can be formed and the probability may be computed.

Referring again to FIG. 2, at decision block 206, if a polyp is not detected, the above process may be repeated, wherein a next optical image is acquired at process block 202, and so on, as desired or as additional optical images are available. However, if a polyp is positively identified, then, at process block 208, an alert or signal may be provided to an operator, indicating a positive polyp identification. The alert or signal may take any suitable shape or form, such as an audible or visual cue. At decision block 210, if all the images have been processed (i.e., the colonoscopy procedure is complete), a report is generated at process block 212, which may take any suitable shape or form. However, if all the images have not been processed at decision block 210, additional optical images are acquired and processed at process block 202 to determine if more positive images can be found.

Specific examples are provided below, illustrative of the above-described polyp detection method. These examples are offered for illustrative purposes only, and are not intended to limit the scope of the present disclosure in any way. Indeed, various modifications of the disclosure in addition to those shown and described herein will become apparent to those skilled in the art from the foregoing description and the following example and fall within the scope of the appended claims.

EXAMPLE

As a non-limiting example, a CVC-ColonDB was used to evaluate the methodology described in the current disclosure, where CVC-ColonDB is the only publicly available polyp database, consisting of 300 colonoscopy images with 20 pedunculated polyps, 180 sessile polyps, and 100 flat polyps. The patch descriptor was evaluated first and then the whole polyp detection system was compared with the state-of-the-art methods.

Feature Evaluation

Figure 9D:
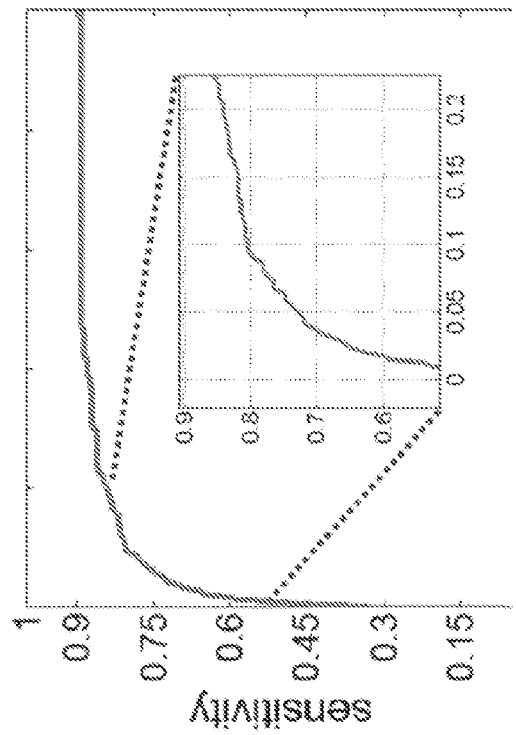
FIG. 9D a graph showing an ROC curve for a polyp detection system according to the present disclosure.
Figure 9C:
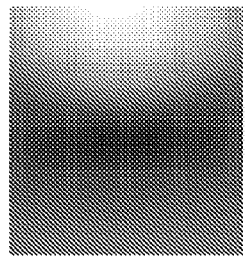
FIG. 9C is an illustration of the average appearance of a polyp boundary revealing informative features.
Figure 9A:
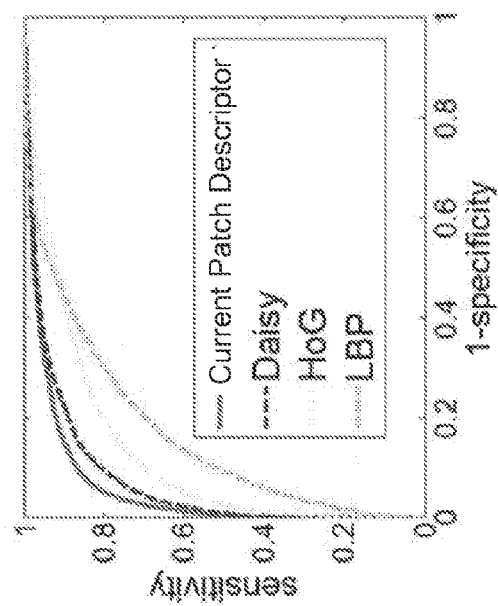
FIG. 9A is a graph comparing resultant ROC curves of an image descriptor using three selected coefficients and ROC curves obtained from other widely-used methods.
Figure 9B:
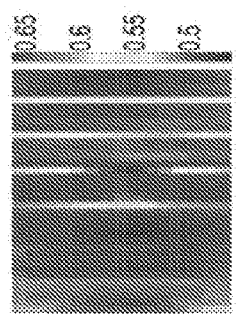
FIG. 9B is an illustration of a discrimination map showing a discrimination power of each feature extracted by the image descriptor across a series of images.

For feature evaluation, 50,000 oriented images around polyp and other boundaries in colonoscopy images were collected. Half of the images corresponding to the first 150 images were selected for training a random forest classifier and used the rest for testing. FIG. 9A compares the resultant ROC curves of the current patch descriptor using three selected coefficients (i.e., 315 features per sub-image) and those obtained from other widely-used methods, such as HoG[1], LBP[2], and Daisy[3]. Due to space constraints, the ROC curves corresponding to more than 3 DCT coefficients were excluded, however the experiments demonstrated that it did not achieve any significant improvement in performance. In terms of running time, the current patch descriptor outperformed the Daisy descriptor. FIG. 9B shows the discrimination power of each feature extracted by the current patch descriptor across all 50,000 images. Comparing the discrimination map against the average appearance of polyp boundary, as shown in FIG. 9C, reveals that the most informative features are extracted from the polyp boundary, indicating that the present descriptor successfully captures the desired image information. FIG. 9D shows the ROC curve for the present polyp detection system.

Voting Scheme and Polyp Detection

For system evaluation, a five-fold cross validation was implemented. To train the two-stage classifier, $N_1=100,000$ oriented image patches were collected from training images with approximately 20,000 samples for each of the five predefined classes, and $N_2=100,000$ oriented image patches were collected with 50% of images being extracted around polyps and the rest around edges in random location in training images. For classification, the random forest classifier was chosen because of its high quality probabilistic output that is utilized in the voting scheme. The trained classification system, followed by the voting scheme, was then applied to the five test folds. The voting scheme detected 267 out of 300 polyps. Thus, outperforming the state-of-the-art, where only 252 candidates were cast inside the polyps.

Figure 10:
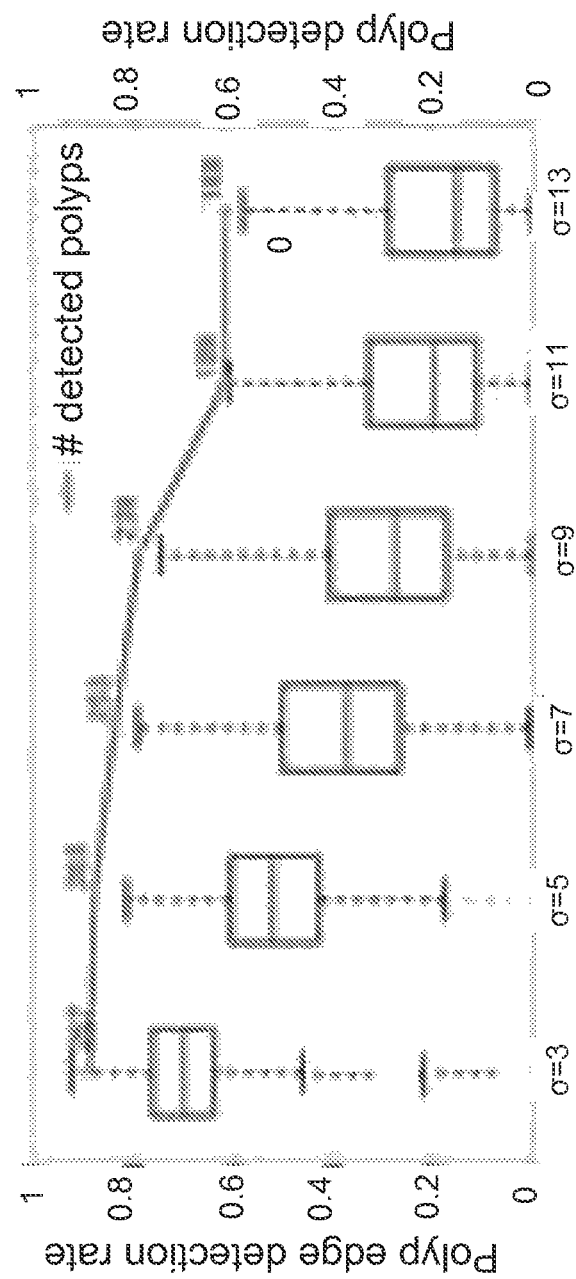
FIG. 10 is a graph showing the effect of Gaussian Smoothing on the sensitivity of a Canny edge detector and the sensitivity of a voting scheme.

Polyps appear in different sizes in colonoscopy images. Because large polyps can often be effortlessly detected by colonoscopists, $\sigma_v$ may be adjusted for detecting polyps of small and moderate sizes. Considering that the area of missed polyps are usually 9 to 16 times smaller than images, $\sigma_v$ may vary between 70 and 90. A detection may be considered as a "true detection" if the maximum of the voting map falls inside the ground truth contour provided in the database. The accuracy of the polyp detection method can be measured by adding the true and false detections generated in the five test folds. For $\sigma_v \in [70, 90]$, the detection point was placed inside 267 polyps and produced 33 false detections which outperforms SA-DOVA descriptor with 252 true and 48 false detections ($p<0.05$, $Z=2.01$). Furthermore, while SA-DOVA descriptor requires five parameters to be tuned, the present disclosure has only two parameters, namely, $\sigma_v$ whose range of variation can be automatically set, and $\sigma_g$, which as shown in FIG. 10 gives comparable performance with changes between 3 and 7.

Figure 11:
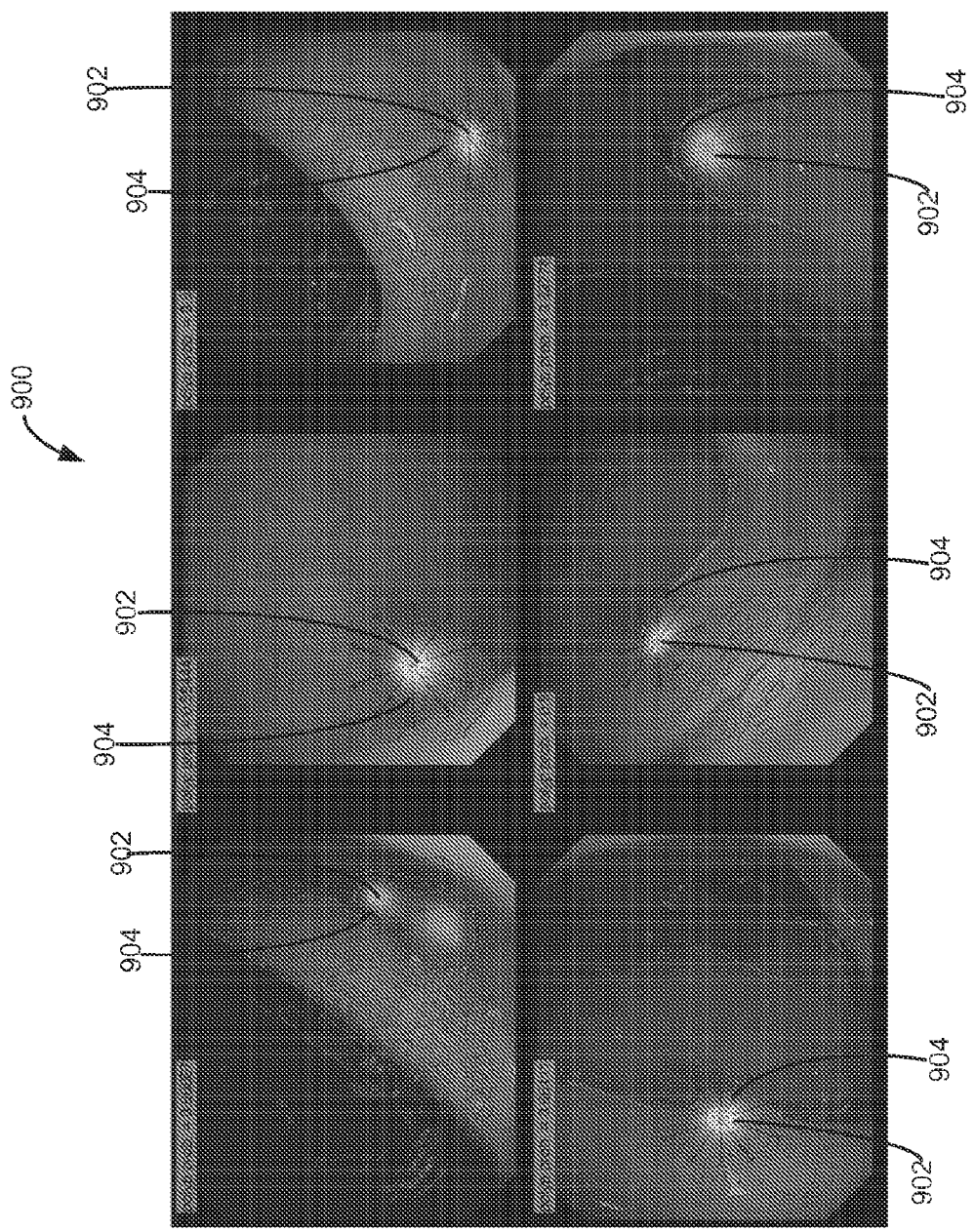
FIG. 11 shows true polyp detection results on voting maps superimposed on colonoscopy images.

Examples of polyp localization are shown in FIG. 11. The voting maps are shown superimposed on the colonoscopy images 900 for better visualization. For each image, the detection point 902 is the maximum of the voting map. The black contour shows the ground truth, and the green pixels 904 are the edges that have passed the classification stage. The false detections mostly occurred in images with no clear boundary between polyps and their surrounding area.

To obtain precision and recall rates, a threshold was changed on the probabilities assigned to the generated polyp candidates. A non-limiting exemplary experiment was conducted to compare one embodiment of the system of the present disclosure with conventional systems. As shown in the table of FIG. 12, the proposed system outperformed previous systems where Haar features, a one-layer classification, and a less accurate voting scheme were employed. Furthermore, the system was evaluated by including 3,000 images that did not contain a polyp (i.e., 300 positive images from CVC-ColonDB and 3000 negative images from a private database).

In a different system evaluation, a five-fold cross validation was implemented to evaluate the polyp detection system using CVC-ColonDB. A detection was "true" if it fell inside the ground truth. As shown in the table of FIG. 13, the proposed system outperformed previous systems in different operating points and yields stable results over a relatively large range of $\sigma$ for precision and recall rates.

Figure 14:
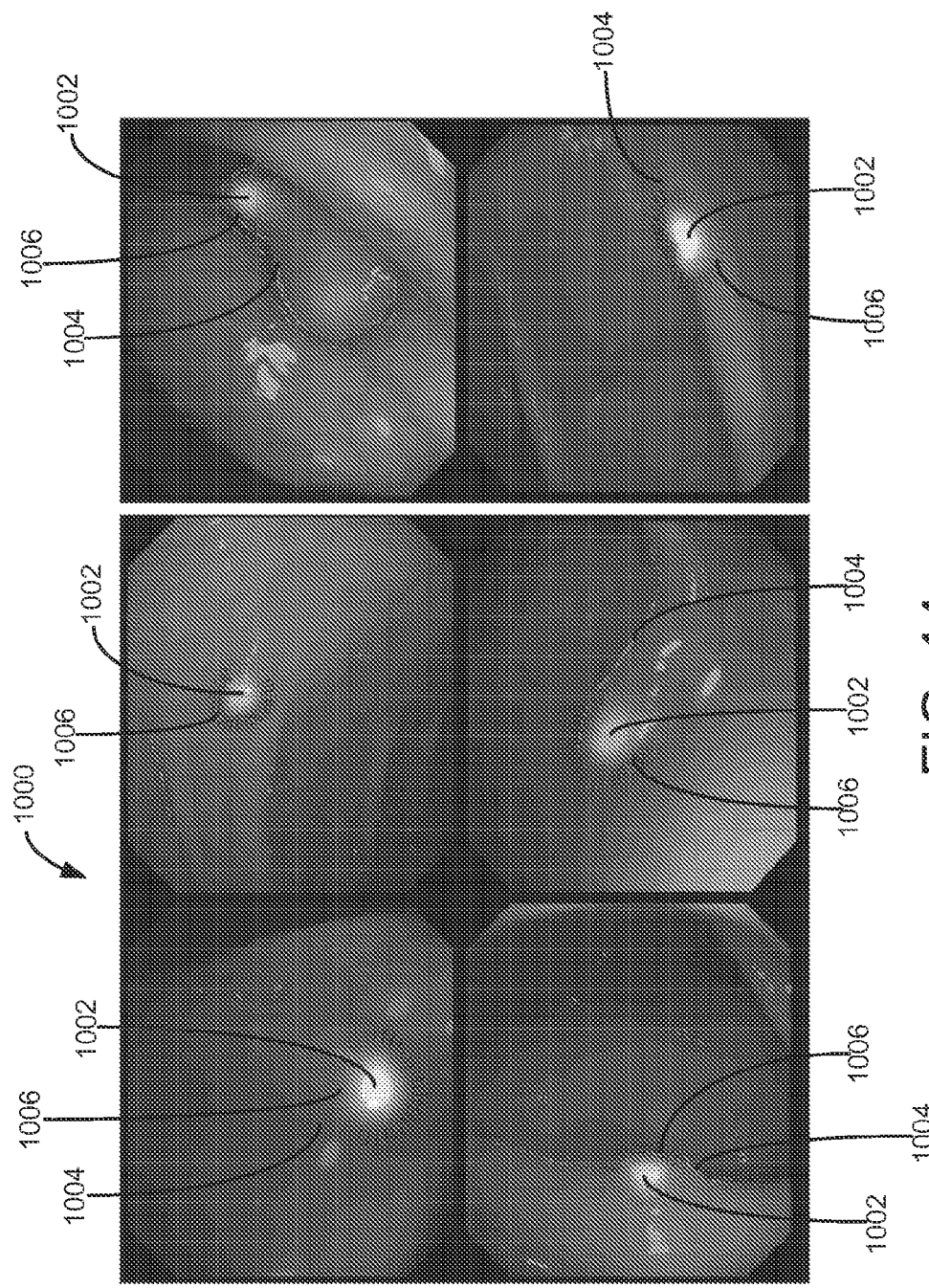
FIG. 14 shows true polyp detection results on voting maps superimposed on colonoscopy images.

Examples of polyp localization are shown in FIG. 14. The voting maps are shown superimposed on the colonoscopy images 1000 for better visualization. For each image, the detection point 1002 is the maximum of the voting map. The black contour shows the ground truth, and the green pixels 1004 are the edges that were retained after the classification stage. Line segments 1006 that reach polyp edges with desired voting directions, are also shown in FIG. 14. False candidates produced by the voting scheme mostly occur due to aggressive edge classification and inadequate clear boundary between polyps and their surrounding area.

Figure 15:
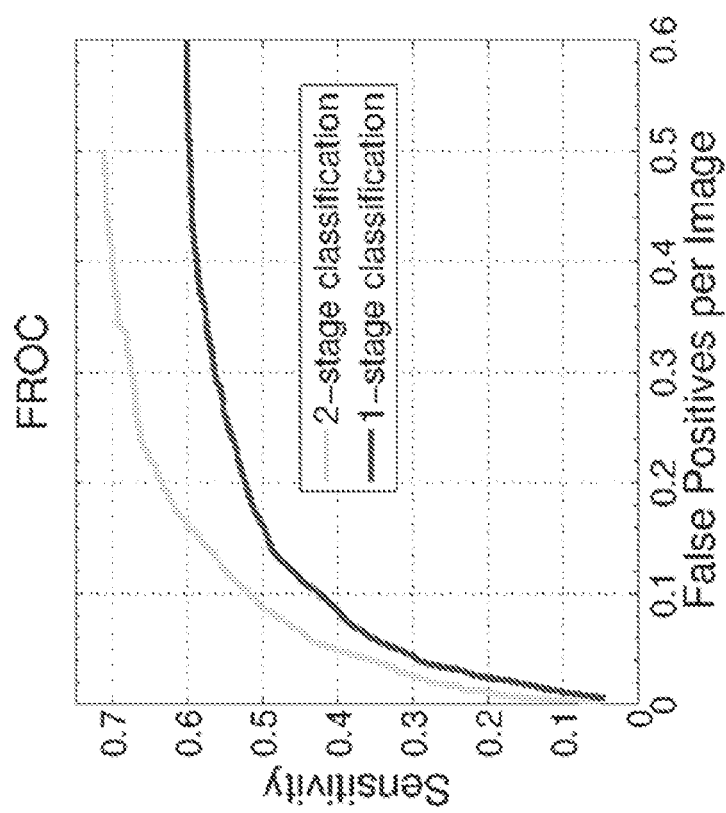
FIG. 15 is a graph comparing resultant ROC curves of a two-stage classification scheme that outperforms a one-stage classification scheme.

The system trained on the entire CVC-ColonDB was further evaluated using eight short colonoscopy videos. The free-response ROC curve, as shown in FIG. 15, demonstrates that the suggested two-stage classification scheme significantly outperforms a one-stage classification scenario where a three class classifier is used for edge classification.

In summary, colorectal cancer most often begins as abnormal growth of the colon wall, commonly referred to as polyps. It has been shown that the timely removal of polyps with optical colonoscopy can reduce the incidence and mortality of colorectal cancer. However, polyp detection with optical colonoscopy is a challenging task and as reported, many polyps remain undetected. Computer-aided detection may offer promises of reducing polyp miss-rate.

The current disclosure describes a system and method that systematically exploits the unique appearance of polyp boundaries to suppress non-polyp edges, yielding a cleaner edge map for the above-described vote accumulation scheme. This approach can accommodate a large variation of polyp shapes, eliminate parallel edge configurations, and enable polyp detection from partially identified boundaries of polyps. Thus, the system and methods disclosed can improve the classification stage by enhancing the feature space with classification systems trained in consistent subspaces of the negative class (i.e., the boundaries of lumen, vessels, and folds, etc.), as well as evaluate the suggested methodology on a significantly larger polyp database.

In addition, the present polyp detection system and method provides feedback to enhance colonoscopists' diagnostic capabilities, especially during long and back-to-back colonoscopies, where human factors, such as insufficient attentiveness and fatigue, result in misdetection of polyps. In addition, the current disclosure describes a method that is not limited to optical colonoscopy and have provided effectiveness for polyp detection in capsule endoscopy.

The present disclosure has been described in terms of one or more exemplary embodiments, and it should be appreciated that many equivalents, alternatives, variations, and modifications, aside from those expressly stated, are possible and within the scope of the disclosure.

We claim:

1. A system for automated polyp detection in optical colonoscopy images, the system comprising:
   an input configured to acquire a series of optical images;
   a processor in communication with the input; and
   a memory containing instructions that, when executed by the processor, causes the processor to perform a process on the series of optical images comprising:
      applying a color filter to create a plurality of color filtered images for each optical image of the series of optical images;

locating a series of edge pixels on at least one of the plurality of color filtered images;

obtaining a plurality of oriented image patches corresponding to each of the series of the edge pixels, the plurality of oriented image patches represented by an intensity signal characterized by at least one of rotation invariance or illumination invariance;

estimating an edge normal for each edge pixel;

constructing at least one classification system corresponding to the plurality of color filtered images, the at least one classification system configured to enhance low level features of the plurality of color filtered images prior to classification;

generating appearance features from a series of feature vectors selected from the at least one classification system;

performing an edge classification threshold analysis on each of the plurality of oriented image patches;

determining, based on the edge classification threshold analysis, that a given image patch is consistent with an edge threshold; and generating a report indicating potential polyps with a vote accumulation greater than a threshold, the vote accumulation including a probabilistic output for each of the potential polyps in the absence of a predefined parametric model.

2. The system of claim 1, wherein the color filter includes a red filter, a green filter, and a blue filter.

3. The system of claim 1, further comprising a Canny edge detection algorithm stored on the memory and applied to the plurality of color filter images when locating the series of edge pixels on at least one of the plurality of color filtered images.

4. The system of claim 1, wherein the edge normal for each of the series of the edge pixels is estimated by a tensor voting with a ball tensor placed at a location of each of the series of edge pixels.

5. The system of claim 1, wherein each of the series of edge pixels are assigned at least one classification score based on an estimated edge normal, wherein when the at least one classification score is less than 0.5, a corresponding edge pixel of the series of edge pixels is eliminated.

6. The system of claim 1, wherein the process further comprises comparing the plurality of oriented image patches and the series of feature vectors when performing the edge classification threshold analysis on each of the plurality of oriented image patches.

7. The system of claim 1, wherein the process further comprises applying a random forest classifier, whereby the edge threshold is in a range of 0.5 to 1.0 when determining, based on the edge classification threshold analysis, that the given image patch is consistent with the edge threshold.

8. The system of claim 1, wherein for each edge pixel in each optical image, the vote accumulation is performed for each of one or more categories to generate a plurality of voting maps.

9. The system of claim 8, wherein the at least one classification system includes a two-stage classification system to filter out non-polyp edges and retain polyp edges around and on a boundary of the polyp.

10. The system of claim 1, wherein the vote accumulation indicates an output for each polyp in absence of a parametric model of polyps by detecting curvy boundaries along the series of edge pixels.

11. A method for automated polyp detection in optical colonoscopy images, the method comprising:

applying a color filter, using a processor in communication with an input configured to acquire a plurality of optical images, to create a plurality of color filtered images for each of the plurality of optical images;

locating a series of edge pixels on at least one of the plurality of color filtered images;

obtaining a plurality of oriented image patches corresponding to each of the series of the edge pixels, the plurality of oriented image patches represented by an intensity signal characterized by at least one of rotation invariance or illumination invariance;

estimating an edge normal for each edge pixel;

constructing at least one classification system corresponding to the plurality of color filtered images, the at least one classification system configured to enhance low level features of the plurality of color filtered images prior to classification;

generating appearance features from a series of feature vectors selected from the at least classification system;

performing an edge classification threshold analysis on each of the plurality of oriented image patches;

determining, based on the edge classification threshold analysis, that a given image patch is consistent with an edge threshold; and generating a report indicating potential polyps with a vote accumulation greater than a threshold, the vote accumulation including a probabilistic output for each of the potential polyps in the absence of a predefined parametric model.

12. The method of claim 11, wherein the color filter includes a red filter, a green filter, and a blue filter.

13. The method of claim 11, wherein locating the series of edge pixels on the at least one of the plurality of color filtered images comprises applying a Canny edge detection algorithm to the plurality of color filter images.

14. The method of claim 11, further comprising estimating the edge normal for each of the series of the edge pixels by a tensor voting with a ball tensor placed at a location of each of the series of edge pixels.

15. The method of claim 11, further comprising assigning at least one classification score to each of the series of edge pixels based on an estimated edge normal, wherein when the at least one classification score is less than 0.5, a corresponding edge pixel of the series of edge pixels is eliminated.

16. The method of claim 11, further comprising comparing the plurality of oriented image patches and the series of feature vectors when performing the edge classification threshold analysis on each of the plurality of oriented image patches.

17. The method of claim 11, further comprising applying a random forest classifier, whereby the edge threshold is in a range of 0.5 to 1.0 when determining, based on the edge classification threshold analysis, that the given image patch is consistent with the edge threshold.

18. The method of claim 11, further comprising performing the vote accumulation for each edge pixel in each optical image for each of one or more categories to generate a plurality of voting maps.

19. The method of claim 18, wherein the at least one classification system includes a two-stage classification system to filter out non-polyp edges and retain polyp edges around and on a boundary of the polyp.

20. The method of claim 11, wherein the vote accumulation indicates an output for each polyp in absence of a parametric model of polyps by detecting curvy boundaries along the series of edge pixels.

* * * * *